United States Patent [19]

Bardos et al.

[11] Patent Number: 4,882,147
[45] Date of Patent: Nov. 21, 1989

[54] NOVEL POLYNUCLEOTIDE ANALOGS, METHODS FOR INHIBITING NUCLEIC ACID POLYMERASES AND METHODS FOR INDUCING SYNTHESIS OF INTERFERON

[75] Inventors: Thomas J. Bardos, Snyder; Yau-Kwan Ho, Williamsville; Steven J. Kasper, Rochester; Robert G. Hughes, Jr., Kenmore, all of N.Y.

[73] Assignee: The Research Foundation of State University of New York, Albany, N.Y.

[21] Appl. No.: 133,524

[22] Filed: Dec. 16, 1987

[51] Int. Cl.⁴ .................... A61K 39/00; A61K 45/02
[52] U.S. Cl. ...................... 424/85.4; 435/91
[58] Field of Search ............... 424/85; 435/91

[56] References Cited

U.S. PATENT DOCUMENTS 3,594,278 7/1971 Naylor ................................ 435/91
3,850,749 11/1974 Kaufmann ........................... 435/91

OTHER PUBLICATIONS

O'Mally, J. A., et al, Molecular Pharmacology, 11, 61–69 (1975).
Vastola, K. A. et al, Research Communications in Chemical Pathology & Pharmacology, vol. 45, No. 3, 407–419 (1984).
Alderfer, J. L. et al, Polymeric Materials in Medication, Gebelein, C. G. et al, Editors, Plenum, New York, 125–138 (1985).

Primary Examiner—Peter D. Rosenberg
Attorney, Agent, or Firm—Howard M. Ellis; Michael L. Dunn

[57] ABSTRACT

Polyribonucleotide analogs which are partially substituted by the introduction of mercapto groups and fluorine at the 5-position of some of their cytosine and uracil bases possess effective in vivo antitumor activity. Double stranded complexes formed from such polynucleotides are especially active as interferon inducers.

22 Claims, No Drawings

NOVEL POLYNUCLEOTIDE ANALOGS, METHODS FOR INHIBITING NUCLEIC ACID POLYMERASES AND METHODS FOR INDUCING SYNTHESIS OF INTERFERON

BACKGROUND OF THE INVENTION

This invention relates generally to novel synthetic polynucleotides which have been chemically modified by the introduction of reactive mercapto groups and also fluorine atoms at the 5-positions of some of the cytosine and uracil bases in their polymeric chains. The partially unsubstituted polynucleotides are useful in blocking the function of nucleic acid polymerases which are essential for the replication of neoplastic mammalian cells. In addition to being potent inhibitors of nucleic acid polymerases, complexes containing the partially substituted polynucleotides also actively induce synthesis of interferon.

Nucleic acid polymerases have been shown to be target enzymes of several anti-cancer drugs. For example, Bardos et al, Vol. 13, page 359, Proceedings of American Association of Cancer Research, first proposed the use of modified polynucleotides containing mercapto groups at the 5-position of some of the pyrimidine bases of the polymeric molecules as inhibitors of nucleic acid polymerases. In general, the early study showed that partially thiolated DNA and RNA isolates, 5-mercaptopolycytidylic acid (MPC) and 5-mercaptopoly-uridylic acid (MPU), were useful as inhibitors of DNA-dependent RNA polymerases, RNA-directed DNA polymerases (reverse transcriptases) and DNA polymerase alpha from regenerating (normal) rat liver.

In addition to the inhibitory antitemplate activity of partially thiolated polynucleotides in a DNA polymerase system, i.e., selective and strong binding to a specific target enzyme in a manner to prevent binding of the natural template or primer required for gene replication or transcription and cell growth, double-stranded polynucleotide complex, poly(inosinic acid)-5-mercaptopolycytidylic acid (PolyI.MPC) has shown to be capable of inducing human alpha, beta and gamma interferons. Both the inhibitory (antitemplate) and interferon inducing properties of such polynucleotide may contribute to its overall favorable antitumor activity.

In contrast to the antitemplate mode of action of partially thiolated polynucleotides, halogenated polynucleotides, such as fluorinated polycytidylic acid (FPC), were found to lack DNA polymerase inhibitory activity. Instead, they appear to exert their cytotoxic effects via some other mechanism. Thus, even though FPC lacks the desired selectivity associated with antitemplate inhibitory polynucleotides it nevertheless has been shown to be actually more cytotoxic than MPC in some in vitro cell culture systems, presumably due to the cytotoxic effect of the monomeric 5-fluorocytidine liberated as a result of the hydrolysis of FPC.

In view of the observation that base compositions of modified heteropolynucleotides appear to have profound effects on the mode of action of antitumor compounds, it would be highly desirable to have compounds which provide a broader spectrum of antitumor activities, such as acting as potent cytoxic agents while also inhibiting replication of tumor cells through the antitemplate mode of action, including those which act on the immunologic system. Accordingly, the present invention provides for novel partially substituted polynucleotides, methods for actively inhibiting the replication of neoplastic cells in the in vivo biological system, including methods for inducing the synthesis of interferon.

SUMMARY OF THE INVENTION

It is a principle object of the present invention to provide for a group of novel synthetic heteropolynucleotides which have been modified by the alternating introduction of mercapto groups and fluorine atoms at the 5-position of some of their cytosine and/or uracil bases. More specifically, one aspect of the invention relates to synthetic partially substituted polyribonucleotides and any of its salts, e.g. sodium, potassium ammonium, cetyltrimethylammonium, derived from either cytidine-5'-phosphate (CMP) or uridine-5'-phosphate (UMP) wherein the nucleotides are linked to one another through 5'→3' phosphodiester bonds forming a polymer chain. The partially substituted polynucleotides of the present invention include in particular 5-mercapto-5-fluoro-poly(cytidylic acid), MFPC, and 5-mercapto-5-fluoro-poly(uridylic acid), MFPU.

A still further object of the present invention is to provide for a group of novel synthetic partially substituted poly(2'-deoxyribonucleotides) and any of its salts, e.g. sodium, potassium, ammonium, cetyltrimethylammonium, derived from the pyrimidine base-containing mononucleotide, 2'-deoxycytidine-5'-phosphate (dCMP) or 2'-deoxyuridine-5'-phosphate (dUMP) also in which some of the hydrogens at the 5-position in the cytosine and uracil bases of their polymeric chains have been substituted with mercapto groups and some others with fluorine atoms. In particular, they include 5-mercapto-5-fluoro-poly(2'-deoxycytidylic acid) and 5-mercapto-5-fluoro-poly(2'-deoxyuridylic acid).

A still further principal object of the present invention is to provide for double stranded polymers containing the foregoing partially substituted polynucleotides complexed with poly(inosinic acid) designated Poly(I), or poly(adenylic acid) designated Poly(A).

A further aspect of the invention relates to methods of inhibiting the replication of neoplastic cells and inducing the synthesis of interferon in an in vivo biological system, and in particular, mammalian cells by exposing susceptible cells to an effective concentration of the partially substituted polynucleotides or polynucleotide complexes.

DETAILED DESCRIPTION OF THE INVENTION

The polynucleotides of the subject invention are heteropolymers in which the hydrogen at the 5-position of some of their pyrimidine bases, cytosine or uracil are substituted with mercapto groups and some are substituted with fluorine. Accordingly, the cytosine and uracil moieties of the mononucleotide residues of polycytidylic acid (PC) and polyuridylic acid (PU) have at the 5-position of each nucleotide unit either hydrogen, mercapto or fluorine. That is to say, from about 5 to about 90 percent by the hydrogens in the 5-position of the (C) or (U) units in the polynucleotide chain are substituted with fluorine, and in addition from about 1 to about 30 percent of the hydrogens in the 5-position of the (C) or (U) chains are substituted with mercapto groups which may be present in their oxidized disulfide form. Thus, the heteropolymers contain hydrogen, mercapto groups and fluorine at the 5-position of their pyrimidine bases.

Preferred polyribonucleotides are designated MFPC and MFPU.

A further preferred embodiment of the synthetic partially substituted heteropolynucleotides are derived from the pyrimidine base-containing mononucleotides, 2'-deoxycytidine-5'-phosphate (dCMP) and 2'-deoxyuridine-5'-phosphate (dUMP). The phosphate groups of such 2'-deoxyribonucleotides link the 5'-hydroxyl of the sugar moiety of the 3'-hydroxyl of the adjacent nucleotide unit in the polymeric chain by forming a phosphodiester linkage with the elimination of a molecule of water. Accordingly, the present invention also contemplates partially substituted 3'→5' poly(2'-deoxyribonucleotides), poly(2'-deoxycytidylic acid (PdC) and poly(2'-deoxyuridylic acid (PdU), derived from the pyrimidine base-containing mononucleotide (dCMP) or (dUMP) in which from about 5 to about 90 percent of the hydrogens in the 5-position of the pyrimidines in the (PdC) or (PdU) chains are substituted with fluorine and in addition from about 1 to about 30 percent of the hydrogens in the 5-position of the pyrimidines in the (PdC) or (PdU) chains are also substituted with mercapto groups which may be present in their oxidized disulfide form. Preferred embodiments may be designated 5-mercapto-5-fluoropolydeoxycytidylic acid and 5-mercapto-5-fluoro-polydeoxyuridylic acid, that is, MFP(dC) and MFP(dU), respectively.

In addition to the single stranded partially substituted polyribonucleotides, MFPC and MFPU, the present invention contemplates novel double stranded polynucleotides. MFPC may be complexed with poly(inosinic acid) in a base ratio of 1:1. In addition, MFPU may be complexed with poly(adenylic acid) in a base ratio of 1:1 or 2:1. The double stranded complexes are active inducers of interferon and also possess antitemplate inhibitory activities in mammalian cells.

In general, the polynucleotides of the invention are prepared by first synthesizing an intermediate partially fluorinated polynucleotide which is then partially thiolated. The partially fluorinated polynucleotides with predetermined base composition may be prepared enzymatically using polynucleotide phosphorylase or terminal deoxynucleotidyl transferase (TdT) which catalyzes the synthesis of polyribonucleotides and poly(2'-deoxyribonucleotides), respectively, having base compositions determined by the ratio of substances used in the reaction mixture.

In preparing the partially fluorinated polynucleotide intermediates the substrates are 5-fluoro substituted and unsubstituted uridine diphosphates or 5-fluoro substituted and unsubstituted 2'-deoxyuridine triphosphates. Alternatively, the substrates are 5-fluoro substituted and unsubstituted cytidine diphosphates or 5-fluoro substituted and unsubstituted 2'-deoxycytidine triphosphates. The specific ratio of 5-fluoro substituted or unsubstituted substrate in each of the above pairs will determine the composition of the resulting partially fluorinated polynucleotide.

According to the following reaction scheme, some of the unsubstituted bases of the partially fluorinated polynucleotides are then thiolated at their 5-positions, or in other words, the partially fluorinated polynucleotide is then also partially thiolated while the 5-fluoro substituted bases in the polymeric chain remain unchanged.

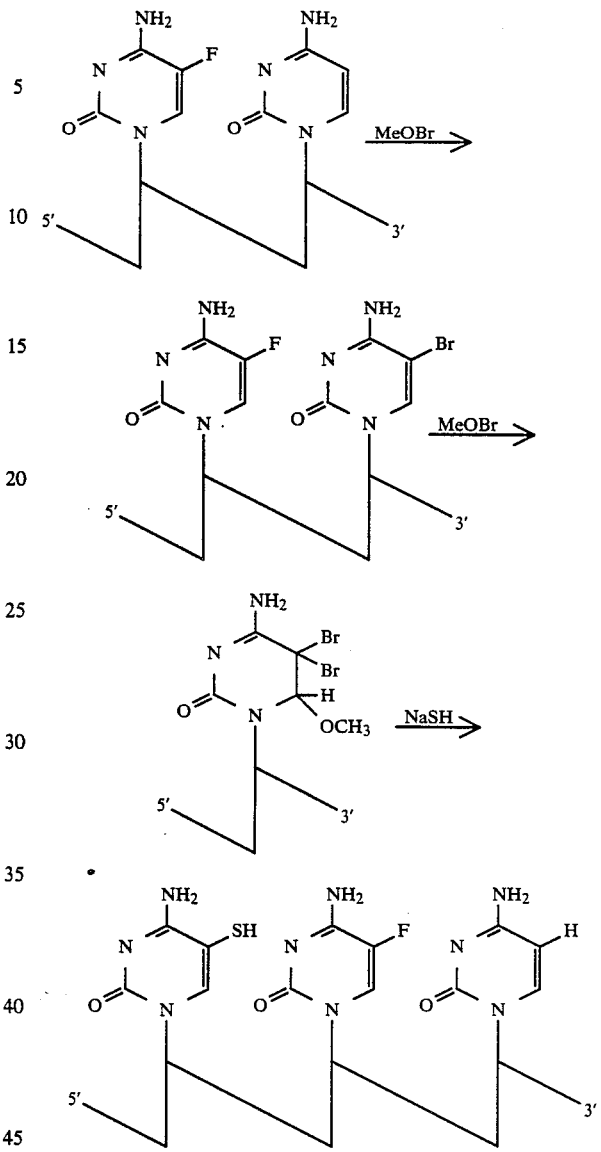

The final partially substituted heteropolynucleotide of the foregoing reaction scheme should be viewed as illustrative only of one possible sequence of mononucleotides. That is to say, the polymer comprising unsubstituted, 5-fluoro substituted and 5-mercapto substituted bases in a chain may be arranged in any number of possible sequences.

As previously indicated, the partially substituted polynucleotides of the invention are active cytotoxic agents, and possess inter-alia antitemplate inhibitory activity and some also appear to exert their antitumor affects through some other mechanism. For instance, MFPC has been found to be an active inhibitor of DNA polymerase alpha from MOLT-4 human lymphoma cells, as well as being cytotoxic to solid tumors, A-549 human lung carcinoma and HT-29 human colon carcinoma cell lines. In addition, MFPC has been shown to be active against NIH 3T3 cells that had been transformed by the human bladder c-Ha ras oncogene, EJ, designated 3JI. The double stranded polynucleotides of the invention are useful as interferon inducers, but in addition poly(I).MFPC has been shown to be active in the inhibition of mouse mammary tumors.

As inhibitors of neoplastic mammalian cells, etc., susceptible cells are exposed to an effective concentration of the partially substituted polynucleotide. In general, an effective concentration will range from about 1 to 60 mg/kg body weight. Interferon inducement in vitro will occur at 2-50 μg/ml concentration. The polynucleotides of the invention are also useful as antifungal agents when administered to susceptible cells in a fungi inhibiting amount.

The actual quantity of the compound administered for treatment of tumors varies depending upon the size of the warm blooded animal involved, upon the type of solid tumor and upon the species of animal involved. In general, for most applications, the effective tumor inhibiting concentration will be within the range indicated above. In general, large animals require less of any pharmaceutical compound per kilogram of body weight than smaller animals. The expression "solid tumors" as used herein are those epithelial neoplasms, such as skin and stomach cancer; connective tissue neoplasms, such as bone and smooth muscle cancer; neoplasms of the nervous system; neoplasms of multiple tissues, such as breast cancer and kidney cancer; and miscellaneous neoplasms such as placenta cancer and ovary carcinoma. Of particular interest herein are the solid cancer tumors of the colon, lung and breast.

Treatment may be by any suitable method which is effective for the particular tumor, i.e., oral, rectal, topical, parenteral, or other routes of administration, as appropriate. The polynucleotides of the invention may be used with pharmaceutically acceptable diluents, extenders, carriers and the like. It is believed that parenteral treatment by intravenous, subcutaneous or intramuscular application, formulated with appropriate carrier or diluent to facilitate application will be the preferred method of administering the polynucleotides of the invention to warm blooded animals.

The following specific examples demonstrate the products and methods of the present invention. However, it is to be understood that these examples are for illustrative purposes only and do not purport to be wholly definitive as to conditions and scope.

EXAMPLE I

Part A: Enzymatic Synthesis of Partially Fluorinated Poly(Cytidylic Acid) (FPC)

A reaction medium of 5 mls contained potassium cytidine disphosphate (Sigma) (10 mM, 0.02303 grams), sodium 5-fluorocytidine diphosphate (10 mM, 0.02403 grams), magnesium chloride (Sigma) (10 mM), EDTA (Sigma) (0.5 mM, pH 6.6); polynucleotide phosphorylase type 15 from *Micrococcus luteus* (Pharmacia) 5 units per ml of reaction mixture), Tris-hydrogen chloride buffer pH 9.0 (0.15M, and 1 ml deionized and distilled water; all in specially treated 15 ml tubes that had been soaked in Tris HCl buffer and thoroughly rinsed with distilled water and made RNase free. This solution was mildly shaken and incubated for 11 hours at 37° C. The polymerization reaction mixture was deproteinated by repeated extractions with chloroform-isoamyl alcohol (24:1 v/v).

The resulting copolymer was isolated by gel filtration. A G-100 Sephadex column was used for purification; it had the following dimensions and specifications: height 87 cm, radius 0.8 cm, equilibrated and eluted with Tris-HCl (20 mM, pH 7.2), at a flow rate of approximately 48 ml/hour. The aqueous phase was placed in the column and fractions collected on a LKB fractionator with U.V. recorder; 3.5 ml fractions in 60 RNase free tubes (washed, heated at 350° C. for 45 minutes) (3.5 ml/tube) were collected. The polynucleotide peak was concentrated via dialysis. Cellophane dialysis tubing (Fisher) of different diameters and various lengths was prepared by soaking in 0.5 percent sodium lauryl sulfate for 5 minutes, boiled in water for 15 minutes and stored in 95 percent ethanol at 4° C. The FPC was transferred to the dialysis bag, sealed and placed in a petri dish, then covered with polyvinyl pyrrolidone at 4° C. The solution was monitored until the appropriate volume of approximately 3 ml was obtained and then it was transferred via Pasteur pipette to an RNase-free vial and stored at 4° C. The unreacted monomers were collected via rotary evaporation and stored at 4° C. The polynucleotide was characterized by UV (Beckman Model 25, Cary 118) and NMR (JEOL 270 MHz) analyses. The NMR work was performed with a fluorine 19-probe in 5 mm RNase free tubes using the sample (FPC) and standard 5-fluorocytidine (Calbiochem) references at 19 mM and 11 mM. The sample FPC, in order to obtain a measurable quantity of fluorine, was reconcentrated via dialysis as previously described to 1.5 ml at 61 mM. 400 scans were run on the standards and 1200 scans were compiled on the polymer. Also, the extinction coefficient was determined by measuring the UV absorbance at 260 mm and the quantity of polynucleotide assayed by phosphate analysis.

Part B: Conversion of FPC Into Its Cetyltrimethylammonium Salt

To 14 ml of the sodium salt of partially fluorinated poly(cytidylic acid) 20.7 mg, 64.12 umole, 4.58 mM) in an aqueous solution of Tris-HCl (20 mM, pH 7.2) at 4° C., 1.52 ml of a 2% aqueous solution of cetyltrimethylammonium bromide (Eastman Kodak) 83.2 umol, a 1.3 fold excess, was added dropwise. The precipitated cetyltrimethylammonium FPC was collected by centrifugation (7000 rpm, 10 min) in a Nalgene 50 ml tube. It was washed with distilled water three times (5 ml). The pellet was transferred to a 100 ml round bottom flask (RNase free) and dissolved in methanol (20 ml) by gentle stirring at 4° C. After 12 hr of stirring not all the precipitate went into solution. The solution was again centrifuged and the supernatant collected. U.V. measurements (Cary 118) of the solution showed an increase in absorbance at 270 nm (72.4 umol). The pellet would not go completely into solution in methanol nor aqueous Tris-HCl buffer. The supernatant was evaporated to dryness via rotary evaporation in vacuo. The residue was dried in vacuo in a dessicator over phosphorus pentoxide for 12 hr at 25° C.

Part C: Formation of Methoxybromide Adducts

Initially methyl hypobromite was prepared. To a mixture of anhydrous methanol (20 ml) and silver carbonate (1.7 g) stirred at −15° C. bromine (dried over $H_2SO_4$) was added (0.14 ml). The solution was vigorously stirred for 1.5 hr at −15° C. The solution was then cooled to −30° C. and filtered through Celilte into a cooled (−15° C.) round bottom flask. The greenish solution (0.128M, $CH_3OBr$), must be used immediately. The dry cetyltrimethylammonium salt of FPC was dissolved in anhydrous methanol (20 ml). For quantitative bromination of the unmodified cytosine residues a 2.2 excess of methoxybromide (141 umoles) was added (1.1 ml, 0.0128M) and the mixture was stirred for thirty minutes at 0° C. The completion of the reaction was determined by the disappearance of the U.V. peak at 270 nm and the coincident appearance of a peak at 234 nm.

Part D: Thiolation of FPC

The halogenated copolymer was rotary evaporated to 10 ml and dry N,N-dimethylacetamide (10 ml) was added and nitrogen was passed through the solution for 15 min. Finely ground NaSH.2H$_2$O in a two-fold excess (14.7 mg, 160 umoles) was rapidly added at 0° C. and the solution was stirred under nitrogen for 1.5 hr. After 1.5 hr the solution was put in an environment of filtered air until the solution turned colorless or for 15 min at 0° C. The thiolated polyribonucleotide (MFPC) was converted into its sodium salt via the dropwise addition of NaCl (3M, 4 ml) at 4° C. The precipitate was collected in a Nalgene centrifuge tube by centrifuging at 7000 rpm for 10 min. The supernatant was discarded and the pellet washed three times with ethanol and NaCl solution (0.15M) 3:1 (v/v), 15 ml each. The resulting partially thiolated and fluorinated poly(cytidylic acid) pellet was dissolved in aqueous Tris-HCl (20 ml, 20 mM, pH 7.2) by stirring gently overnight at 4° C. Not all the MFPC dissolved even after heating at 40° C. for one hour. The copolymer was centrifuged (8000 rpm, 10 min) and the supernatant purified on a column of Sephadex G-100. The pellet contained an insignificant quantity of polymer and was discarded. Spectral analysis of the supernatant was performed on Beckman Model 25 and Gilford 2400-S before gel filtration. The dimensions of the column, eluent and collection procedures were the same as those described for the synthesis of FPC. The supernatant containing MFPC was divided into three equal fractions for gel filtration in order to prevent overloading of the column. The fractions representing MFPC polyribonucleotides were pooled and analyzed spectrophotometrically. The MFPC was then concentrated via cellophane dialysis bags using polyvinyl pyrrolidone at 4° C. to approximately 8 ml and transferred to an RNase free vial.

EXAMPLE II

Preparation of Poly(I).MFPC

Equal molar quantities of Poly(I) and of MFPC were annealed using standard procedure. Thus, 10 ml of a 4 mm solution of Poly(I) and 10 ml of a 4 mm solution of MFPC were mixed together in a sodium phosphate buffer, 20 mm, pH 7.2 containing 0.1M sodium chloride and 2 mm magnesium chloride. The solution was incubated at 25° C. for three hours and at 4° C. for sixteen hours to ensure complete annealing.

The Poly(I).MFPC solution thus obtained was further analyzed by ultraviolet absorption spectrum and its thermal stability determined by the ultraviolet absorption-temperature profile.

EXAMPLE III

The partially 5-thiolated, partially 5-fluorinated poly(cytidylic acid) (MFPC) of Example I was tested in-vitro for its ability to inhibit the growth of cultured cells. The three cells tested were human lung tumor cell line, A549; quasi-normal mouse cell line, NIH 3T3; and NIH 3T3 cells that had been transformed by the human bladder c-Ha ras oncogene, EJ. This clonal line is designated 3JI. 8×10$^3$ cells of A549, 3T3 and 3JI were seeded into 16 mm diameter culture vessels in 0.5 ml aliquots of Eagle Medium containing 10% calf serum (EM10C). The following day, medium was replaced with that containing the indicated concentrations of MFPC noted below in Table I. Cells were trypsinized and counted 7 days post-seeding.

TABLE I

| MFPC (ug per ml) | Cells per dish (% inhibition)* | | |
|---|---|---|---|
| | A549 | 3T3 | 3JI |
| 1 | 0 (100) | 0 (100) | 0 (100) |
| 0.3 | 2.3 × 10$^4$ (90) | 0 (100) | 0 (100) |
| 0.1 | 9.2 × 10$^4$ (62) | 7.0 × 10$^3$ (59) | 4.0 × 10$^3$ (88) |
| 0.03 | 1.6 × 10$^5$ (33) | 1.0 × 10$^4$ (41) | 4.0 × 10$^3$ (88) |
| 0.01 | 1.9 × 10$^5$ (21) | 1.1 × 10$^4$ (35) | 7.0 × 10$^3$ (79) |
| 0.003 | 1.2 × 10$^5$ (50) | 5.0 × 10$^3$ (71) | 7.0 × 10$^2$ (98) |
| 0.001 | 2.2 × 10$^5$ (8) | 1.8 × 10$^4$ (−6) | 2.5 × 10$^4$ (24) |
| 0 | 2.4 × 10$^5$ (0) | 1.7 × 10$^4$ (0) | 3.3 × 10$^4$ (0) |

*The number of cells per dish represents the net increase obtained by substracting the number of cells seeded from the number of cells counted MFPC was found to inhibit each of the foregoing three cell lines with concentrations sufficient to inhibit growth by 50% (IC$_{50}$) ranging from less than 0.003 to about 0.1 ug per ml over a number of experiments. A549 and NIH 3T3 cells had similar sensitivities but were more resistant to MFPC than were the 3JI cells.

EXAMPLE IV

Poly(I).MFPC complex was prepared according to the method of Example II was tested for its ability to inhibit tumor formation by 3JI cells in Balb/C mice. The test animals were injected subcutaneously between the scapula with 1×10$^6$ 3JI cells Beginning the day following tumor implantation, the mice were injected subcutaneously at the tumor site with the indicated amount of Poly(I).MFPC. Injections were given every other day for a total of 8 injections. Control animals were treated with Puck's G saline. Animals were killed three days after the last injection (18 days after tumor implantation) and weighed. Tumors were excised and weighed. The results of the in vivo testing are provided in Table II below.

TABLE II

| MFPC:pI (mg per kg) | No. of mice | Average weight of tumor (g) ± S.D. | Average weight of mice (g) ± S.D. |
|---|---|---|---|
| 0 | 5 | 4.79 ± 2.76 | 27.9 ± 1.5 |
| 5 | 5 | 3.59 ± 2.35 | 27.2 ± 1.5 |
| 20 | 4* | 0.57 ± 0.36 | 14.1 ± 0.9 |

*One mouse died during the course of treatment

The data in Table II shows that Poly(I).MFPC at 20 mg per kilogram body weight greatly inhibited growth of the tumor. It is believed that at lower dosages the inhibitory activity of the polynucleotide complex will be comparable, but with lower potential for toxicity.

EXAMPLE V

A series of in vivo tests were conducted to show on a comparative basis the antitumor activity of Poly-(I).MFPC and Poly(I).MPC in mice. The MFPC used in the study was shown to contain 8% 5-mercaptocytidylate, 33% 5-fluorocytidylate and 49% cytidylate. A stable double helix with Poly(I) was formed. The MPC employed in this study contained 12% 5-mercaptocytidylate residues.

The tumor model used was the SMT-F tumor, a fast growing spontaneous mouse mammary tumor sublined, transplanted subcutaneously to female DBA/2 Jackson mice. Small pieces of tumor (1.5 mm$^2$) and a donor mouse were transplanted with an 18 gauge trocar to the recipient mice which were 8 weeks old and weighed approximately 20 grams each. The Poly(I).MFPC double stranded compound was administered to the mice by subcutaneous injection at the same site of tumor transplantation at a dose of 20 mg/kg body weight on Day 1, Day 7 and Day 13 after transplantation of the tumor. Control mice were given the same volume of saline solution. Tumors were detectable on Day 5 and measurable on Day 7. Tumor size was measured across the largest diameter (length) and its perpendicular diameter (width) with a vernier caliper every other day and expressed as $l \times w$ (mm$^2$). At the end of the experiment, the mice was sacrificed, the tumor excised and weighed. Mean tumor size and weight per group, standard deviations, and standard errors were calculated, analyzed and compared using Student's test.

TABLE III

IN VIVO ANTITUMOR EFFECT OF POLY(I).MFPC

| Agent | Tumor Weight (g) mean ± standard error | % T/C |
|---|---|---|
| Saline | 0.61 ± 0.11 | 100 |
| Poly(I).MFPC | 0.013 ± 0.0061 | 2.06 |
| Poly(I).MPC | 0.14 ± 0.033 | 23.6 |

Three out of five mice treated with Poly(I).MFPC were free of tumor, and they were healthy and normal in appearance. On Day 25, one of these three mice showed a detectable tumor which grew so big that a week later the mouse had to be sacrificed. The other two mice were still free of tumor on Day 32. One out of the 5 mice in the Poly(I).MPC treated group was free of tumor on Day 32.

Although both Poly(I).MFPC and Poly(I).MPC were inhibitory to the growth of tumor in mice, Poly(I).MFPC was more potent (T/C=98) than Poly(I).MPC (T/C=74).

While the invention has been described in conjunction with specific examples thereof, this is illustrative only. Accordingly, many alternatives, modifications and variations will be apparent to persons skilled in the art in light of the foregoing description, and it is therefore intended to embrace all such alternatives, modifications and variations as to fall within the spirit and broad scope of the appended claims.

We claim:

1. A partially substituted 3'→5' polyribonucleotide or salts thereof comprising a polymeric chain derived from a pyrimidine base-containing mononucleotide selected from the group consisting of cytidine-5'-phosphoric acid (CMP) and a uridine-5'-phosphate (UMP) in which from about 5 to about 90 percent of the hydrogens in the 5-position of the pyrimidines in the polymer chains are substituted with fluorine and in addition from about 1 to about 30 percent of the hydrogens in the 5-position of the pyrimidines in the polymer chains are substituted with mercapto groups which may be present in their oxidized disulfide form.

2. The partially substituted polyribonucleotide of claim 1 which is a 5-mercapto-5-fluoro-poly(cytidylic acid).

3. The partially substituted polyribonucleotide of claim 1 which is a 5-mercapto-5-fluoro-poly(uridylic acid).

4. The partially substituted polyribonucleotide of claim 2 complexed with poly(inosinic acid) in a base ratio of 1:1.

5. The partially substituted polyribonucleotide of claim 3 complexed with poly(adenylic acid) in a base ratio of 1:1.

6. The partially substituted polyribonucleotide of claim 3 complexed with poly(adenylic acid) in a base ratio of 2:1.

7. A partially substituted 3'→5' poly(2'-deoxyribonucleotide) or salts thereof comprising a polymeric chain derived from a pyrimidine base-containing mononucleotide selected from the group consisting of 2'-deoxycytidine-5'-phosphate (dCMP) and 2'-deoxyuridine-5'-phosphate (dUMP) in which from about 5 to about 90 percent of the hydrogens in the 5-position of the pyrimidines in the polymer chains are substituted with fluorine and in addition from about 1 to about 30 percent of the hydrogens in the 5-position of the pyrimidines in the polymer chains are substituted with mercapto groups which may be present in their oxidized disulfide form.

8. The partially substituted poly(2'-deoxyribonucleotide) of claim 7 which is a 5-mercapto-5-fluoro-poly(2'-deoxycytidylic acid).

9. The partially substituted poly(2'-deoxyribonucleotide) of claim 7 which is a 5-mercapto-5-fluoro-poly(2'-deoxyuridylic acid).

10. A method of inhibiting the replication of neoplastic mammalian cells by blocking the function of their nucleic acid polymerases which comprises exposing susceptible cells to an effective concentration of the polynucleotide of claim 1.

11. A method of inhibiting the replication of neoplastic mammalian cells by blocking the function of their nucleic acid polymerases which comprises exposing susceptible cells to an effective concentration of the polynucleotide of claim 2.

12. A method of inhibiting the replication of neoplastic mammalian cells by blocking the function of their nucleic acid polymerases which comprises exposing susceptible cells to an effective concentration of the polynucleotide of claim 3.

13. A method of inhibiting the replication of neoplastic mammalian cells by blocking the function of their nucleic acid polymerases which comprises exposing susceptible cells to an effective concentration of the polynucleotide of claim 7.

14. A method of inducing the synthesis of interferon by mammalian cells which comprises exposing susceptible cells to an effective concentration of the polynucleotide complex of claim 4.

15. A method of inducing the synthesis of interferon by mammalian cells which comprises exposing susceptible cells to an effective concentration of the polynucleotide complex of claim 5.

16. A method of inducing the synthesis of interferon by mammalian cells which comprises exposing susceptible cells to an effective concentration of the polynucleotide complex of claim 6.

17. A composition comprising a pharmaceutically acceptable carrier and an antitumor amount of the partially substituted polyribonucleotide of claim 1.

18. A composition comprising a pharmaceutically acceptable carrier and an antitumor amount of the partially substituted polyribonucleotide of claim 2.

19. A composition comprising a pharmaceutically acceptable carrier and an antitumor amount of the partially substituted polyribonucleotide in claim 3.

20. A composition comprising a pharmaceutically acceptable carrier and an interferon inducing amount of the complex of claim 4.

21. A composition comprising a pharmaceutically acceptable carrier and an interferon inducing amount of the complex of claim 5.

22. A composition comprising a pharmaceutically acceptable carrier and an interferon inducing amount of the complex of claim 6.

* * * * *